(12) United States Patent
Moreas et al.

(10) Patent No.: US 7,164,955 B2
(45) Date of Patent: Jan. 16, 2007

(54) METHOD FOR ONLINE CHARACTERIZATION OF A MOVING SURFACE AND DEVICE THEREFOR

(75) Inventors: Geneviève Moreas, Wanze (BE); Yves Hardy, Ougree (BE); Marc Schyns, Roclenge-sur-Geer (BE)

(73) Assignee: Centre de Recherches Metallurgiques, A.S.B.L., Brussels (BE)

( * ) Notice: Subject to any disclaimer, the term of this patent is extended or adjusted under 35 U.S.C. 154(b) by 882 days.

(21) Appl. No.: 10/343,839

(22) PCT Filed: Apr. 17, 2002

(86) PCT No.: PCT/BE02/00055

§ 371 (c)(1),
(2), (4) Date: Feb. 12, 2003

(87) PCT Pub. No.: WO02/101366

PCT Pub. Date: Dec. 19, 2002

(65) Prior Publication Data

US 2003/0182013 A1 Sep. 25, 2003

(30) Foreign Application Priority Data

Jun. 13, 2001 (BE) .................................. 2001/0398

(51) Int. Cl.
*G05B 19/18* (2006.01)
*G01B 11/00* (2006.01)
*G01N 21/00* (2006.01)
*G06F 7/60* (2006.01)
*G06E 3/00* (2006.01)

(52) U.S. Cl. .................. 700/59; 359/107; 356/396; 356/242.1; 703/2

(58) Field of Classification Search .................. 700/59; 703/2; 356/396, 242.1
See application file for complete search history.

(56) References Cited

U.S. PATENT DOCUMENTS 4,417,149 A  11/1983  Takeuchi et al. ............ 250/563
6,206,986 B1  3/2001  Brisberger .................. 148/508

FOREIGN PATENT DOCUMENTS

BE  1005960  4/1994
EP  0557558  9/1993

*Primary Examiner*—Anthony Knight
*Assistant Examiner*—Sunray Chang
(74) *Attorney, Agent, or Firm*—Jacobson Holman PLLC (57) ABSTRACT

The process for the on-line characterization of a surface in motion, preferably a galvannealed sheet, essentially comprises an industrial microscope associated with a stroboscopic laser illumination device, a positioning assembly, an assembly for acquiring and processing images. The obtained view fields vary between 125 µm and 2000 µm in width, the spatial resolution is at least 0.5 µm, and the focussing of the system is precise to a micrometer. The images are taken on a product moving at a speed of between 1 m/s and 20 m/s and are frozen by the use of a stroboscopic illumination device with a duration of illumination of at least 10 ns. The obtained images are processed in several steps. A background average level is first of all regularly evaluated in order to be eliminated from each current image. The processed image is then divided into several zones. The sharpness of each zone is evaluated and stored in memory. A total sharpness coefficient is likewise calculated in order to weight the results subsequently obtained. An operation of binarisation is carried out on the same image using the maximum entropy method in order to detect a maximum number of objects in the image.

In the case of a galvannealed steel strip, any object with a center of gravity belonging to a zone in which the sharpness coefficient is too low is eliminated. The objects are classified into very large, large, small and crystalline, the unclassified ones being eliminated. The crystalline objects are those that have a sufficient ratio of height to width. A correlation function established by calibration then supplies the iron percentage present in the coating (correlation: 0.85).

18 Claims, 4 Drawing Sheets

METHOD FOR ONLINE CHARACTERIZATION OF A MOVING SURFACE AND DEVICE THEREFOR

This is a nationalization of PCT/BE02/00055 filed Apr. 17, 2002 and published in French.

TECHNICAL FIELD

The present invention relates to a process for the on-line characterisation of a surface in motion, in particular the surface of a strip of steel in continuous motion that has undergone a galvannealing treatment, as well as to a device for implementing it.

The invention stands within the context of the development of means for the on line monitoring of industrial processes, i.e. at the very moment of the operation and preferably continuously and in real time, as opposed to checks performed from time to time and a posteriori and the results of which are merely used to adapt the operating parameters of the subsequent products with a view to obtaining precise characteristics and a fortiori to avoiding the defects observed during checks.

The present method may be used in a large number of manufacturing processes, especially metallurgical processes, whether to directly monitor the surface characteristics of the products obtained, as in the case of rolled or coated strips, or to monitor the state of the equipment used, as in the case of mill rolls.

In the following text, the description of the process for the characterisation of a surface, which is the subject matter of the present invention, is centred on the manufacturing of a steel strip subjected to an operation of galvanisation followed by an operation of annealing, commonly referred to as a "strip treated by galvannealing", but this in no way restricts the scope of the invention, which can also be applied within the context of other manufacturing processes, including those mentioned above.

PRIOR ART

It is well known that steel is a prime construction material for numerous application fields. Its high mechanical strength and its great suitability for forming, welding and for application of protective or decorative coatings are properties whose technical significance has long been recognised. Moreover, its advantageous cost price and the ease with which it can be recycled likewise make it of economic interest.

In particular, steel is very widely used in the automotive construction, where the recent development of high-strength steels has allowed to contribute to the reduction of the weight of vehicles and thus to a better protection of the environment, especially by way of reducing fuel consumption and hence the associated pollutant emissions.

However, steel is subject to corrosion because of various aggressive substances, in particular de-icing salts in the case of motor vehicles, and it must be protected in order to maintain its resistance properties for many years.

Among the numerous materials used to protect steel against corrosion, zinc has proven to be of particular interest, in particular owing to its sacrificial behaviour, which is well known to those skilled in the art. On the industrial level, two main techniques are currently used for depositing zinc on steel, namely the electrolytic deposition and the immersion method, referred to as "hot" or "dip" immersion.

Within the context of the automotive industry, it will be observed that not only are the requirements of motor vehicles moving towards increasingly more resistant and thinner sheets in order to reduce the weight of the vehicles but that, in addition, the zinc coatings used in the vehicle are often alloyed with the iron in the steel in order to obtain an Fe—Zn coating that is more suitable for welding and painting and that is providing better anti-corrosion performance.

These coatings of zinc or zinc alloys are applied by means of a succession of steps, which may be summarised as follows:

continuous recrystallisation annealing of the sheet in order to confer upon it the mechanical properties required for its final use and to prepare the surface chemistry of the sheet to make it compatible with the subsequent step of hot dip galvanisation and a step involving hot-dip galvanisation in a bath of molten zinc or zinc alloy containing less than 0.25% of aluminium;

finally, a layer of Fe—Zn alloy may be formed by annealing for the purpose of alloying, hence the name "galvanneal" or "galvannealing" for the treatment (for "galvanising+annealing").

This annealing for the purpose of alloying, which is now widely used, consists in reheating a galvanised strip immediately after it emerges from the coating bath so as to bring about a phenomenon of diffusion annealing between the deposited zinc layer and the iron of the substrate in such a way as to obtain an iron-zinc alloy generally containing between 7 and 13% of iron and ideally between 9 and 11.5%.

After undergoing galvannealed coating, the steel has good paint adhesion, high resistance to corrosion and good weldability, especially when spot-welding.

However, it will be noted that said galvannealed steel is not always free from defects, such as powdering or flaking when it is subjected to press forming. These defects are directly linked to the composition and structure of the Fe—Zn intermetallic compounds formed during the reheating phase of the manufacturing process of the galvannealed product. The kinetics of formation and growth of these various phases (Fe—Zn, Fe—Al or Fe—Al—Zn) are linked to the parameters defining the operating conditions, such as the chemical composition of the steel forming the treated substrate, the chemical composition of the coating bath and the characteristics of the heating cycle, namely time, temperature and evolution of the latter over time.

Given the above elements, optimum monitoring of the galvannealing process would require a knowledge in real time of the characteristics of the coating formed on the steel surface, possibly while considering the content of iron in the alloy formed at the surface as analysed parameter.

This approach, which is based on the on-line determination of the iron level, has been largely developed, especially with respect to the sensors, x-ray gauges and other elements, without for all that arriving at a solution giving acceptable and reliable results when implemented in the context of the industrial production of galvannealed steel strips.

Most of the research in this area is directed at modelling the growth kinetics in the level of iron in the alloy formed at the surface of the galvannealed steel, doing so as a function of the applied thermal cycle. The algorithms derived from this approach allow to monitor the galvannealing operation by performing one or more temperature measurements during the heating cycle carried out during said operation and by correlating the measured value or values with the level of iron that is supposed to have been obtained while taking account of other parameters representative of the industrial line under investigation, said parameters being included in the monitoring algorithm derived from the modelling of said line.

This method is relatively easy in the final phase of the galvannealing process, i.e. when the alloy has been formed, which corresponds to a high emissivity $\epsilon$ of the sheet ($\epsilon$>0.7), but is very difficult to implement in the first half of the heating cycle, in which the emissivity $\epsilon$ is very low ($\epsilon$<0.3), the galvanised sheet being very shiny. The above method still depends on an indirect monitoring based on localised measurements performed in a laboratory and does not allow rapid checking of the galvannealing operation with a view to limiting waste on an industrial line.

Presentation of the Invention

The present invention aims to propose a process based on an innovative approach since it implements the analysis of images obtained by the microscopic visual observation of the surface of the steel strip undergoing the galvannealing process. The underlying principle of the assembly required to obtain the images in question is known per se and is described in the following publication:

Characterisation of Galvannealed Strip.
Moreas, G; Hardy, Y
Centre de Recherches Metallurgiques (Belgium)
Advanced Sensors for Metals Processing Aug. 15–27, 1999
ISSN: 0-919086-92-6

The characterisation process, which is the subject matter of the present invention, does not have the above-mentioned disadvantages that are linked to an indirect monitoring and allows to obtain, after processing of the image obtained by microscopic visualisation, a signal that is proportional to the iron level, or even directly proportional to the powdering level, the two variables being strongly correlated, and to achieve this in a simple and economical manner without prejudicing the productivity of the existing coating lines, on which it can easily be implemented.

Moreover, the process of the invention also allows to directly characterise the Fe—Zn phase appearing at the surface and to store it in the form of an image file.

With a view to allowing easy understanding of the description of the present invention, reference will be made to FIGS. 1, 2, 3 and 4, of which, respectively.

Figure 1:
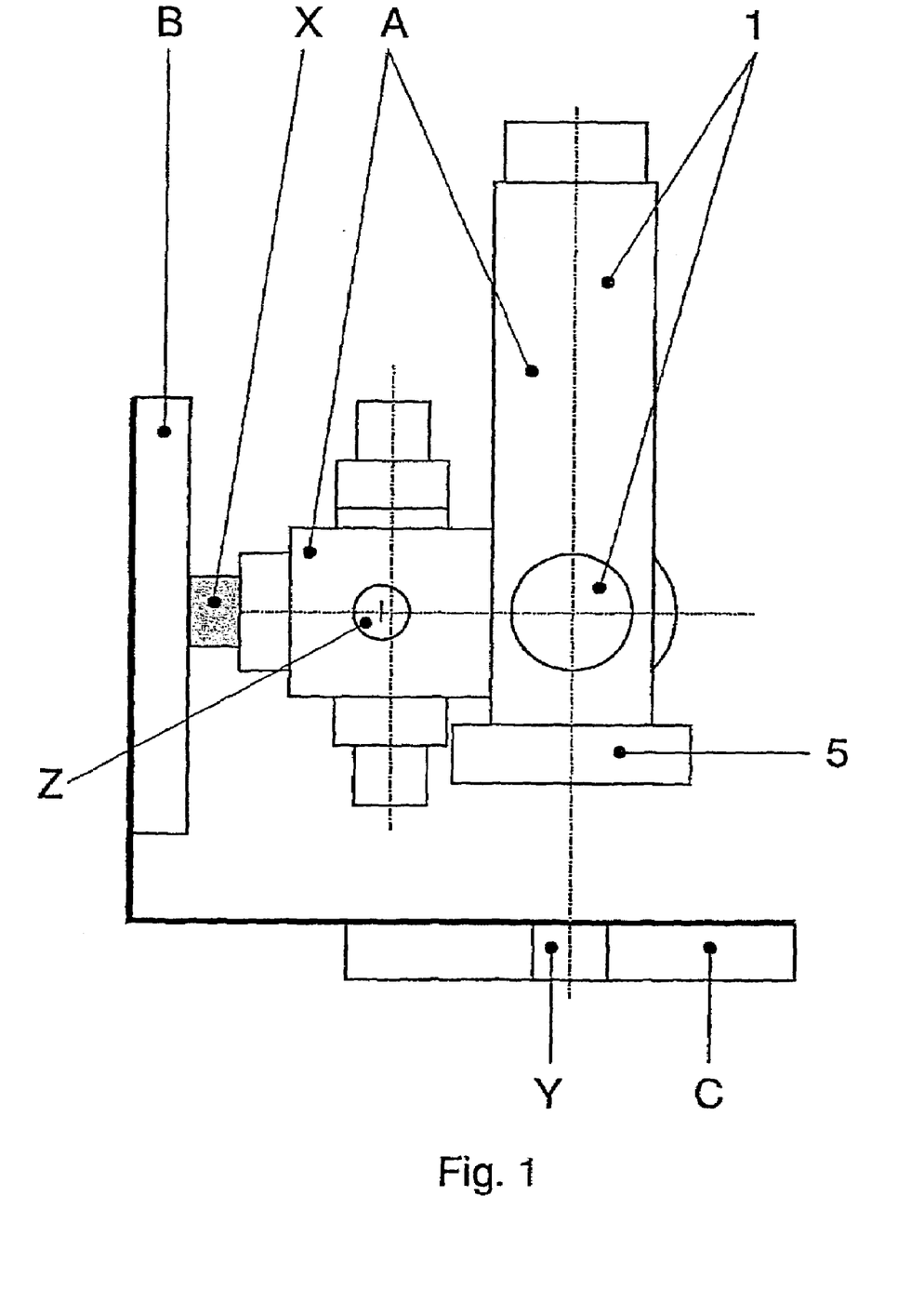
FIG. 1 is a diagrammatic representation in elevation of the assembly used to implement the process of the invention.
Figure 2:
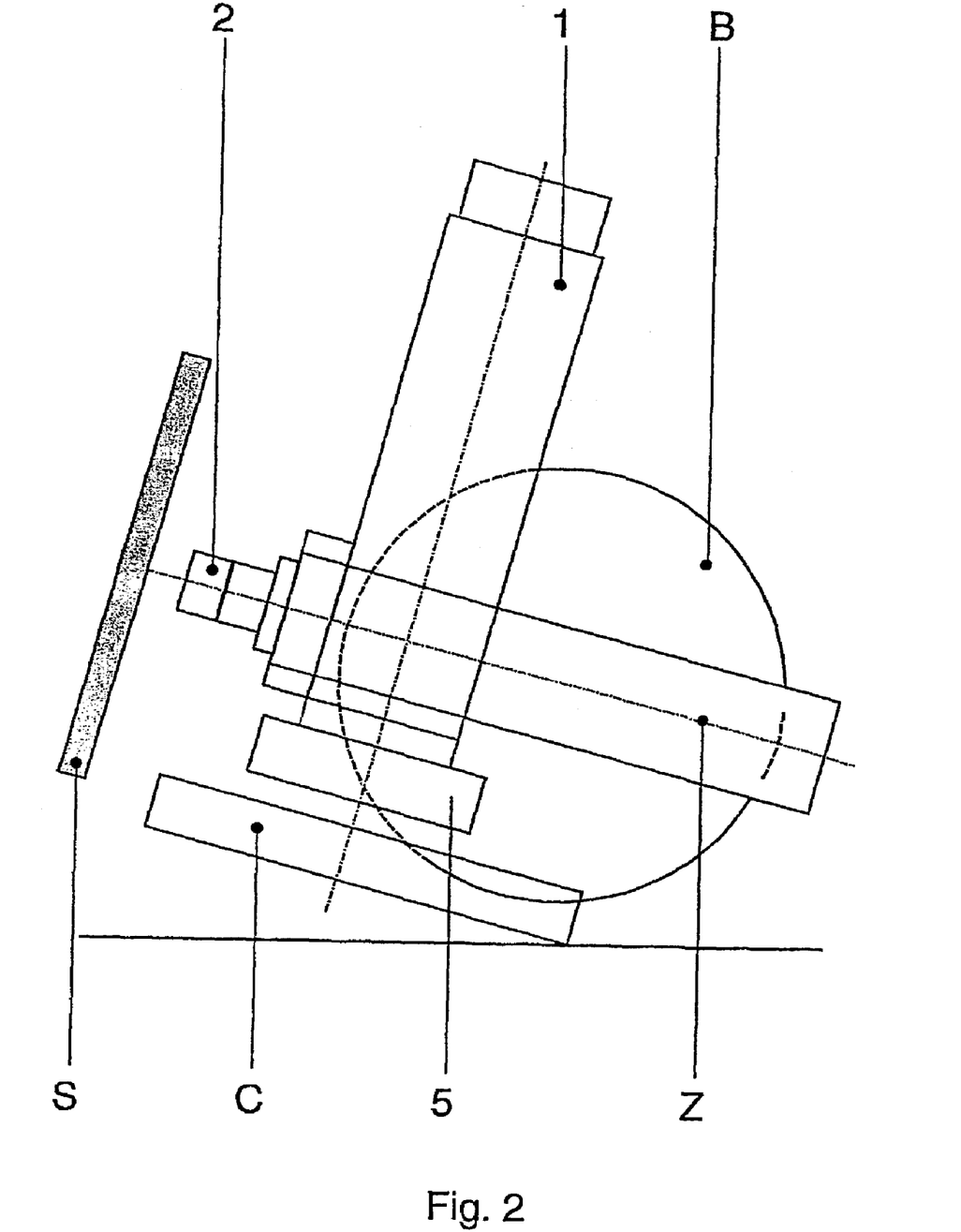
FIG. 2 is a diagrammatic profile representation of the same assembly as that in FIG. 1.
Figure 3:
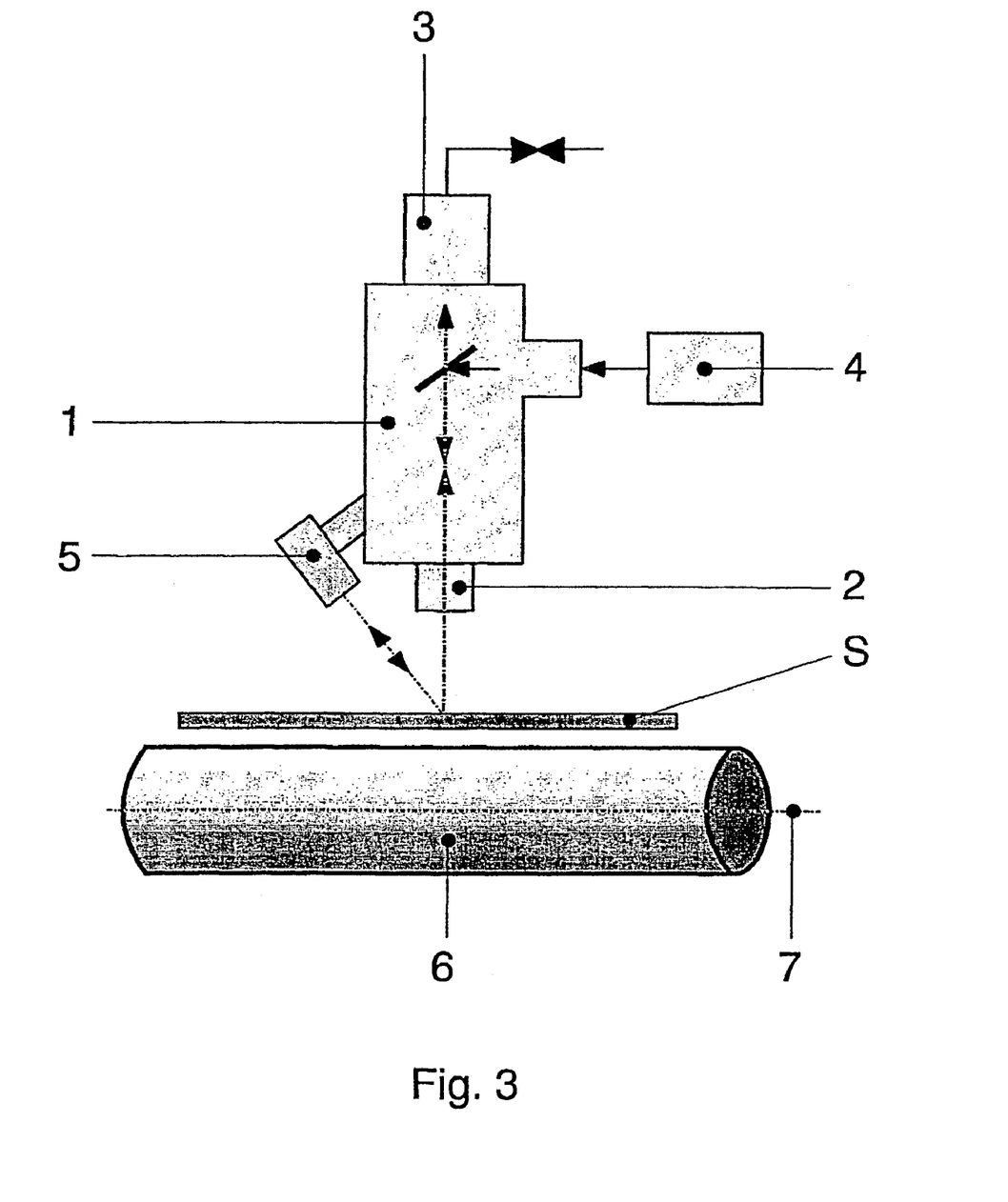
FIG. 3 is the schematic operating diagram of the assembly used to implement the process of the invention.

In accordance with the present invention, a process for the on-line characterisation of a surface (S) in motion, preferably a galvanised sheet, principally implementing:

a first assembly referred to as assembly A, consisting of at least one industrial microscope (1) equipped with an objective (2) that has a long working distance, preferably >5 mm, a camera adaptation lens, a camera with an analog or digital output, such as a CCD camera (3) for example, an illumination device of the bright field type and/or of the dark-field type comprising a laser (4), a distance sensor (5) and a motor acting on the displacement along the (Z) axis, i.e. the displacement along the optical axis of the microscope in order to allow correct focussing of the system, said assembly A being mounted on an assembly referred to as assembly D, which comprises two elements (B) and (C), rotation tables (B) and (C) for instance, said assembly D allowing to position the optical axis, i.e. (Z), perpendicularly to the plane comprising the surface (S) under observation, said means preferably consists in at least two motor-driven rotation tables (B) and (C) allowing, by their joint action, to position the optical axis (Z) of the microscope perpendicularly to the observation plane comprising the surface (S) under examination, the assembly D carrying the assembly A being possibly provided with an anti vibration system, allowing to isolate said assembly from the metal frame, as found on an industrial continuous annealing and galvanisation line, which has to support it and is subjected to the various vibrations that are often present in this type of industrial process;

an assembly of means, preferably comprising a computer that allows to carry out at least the following operations:

monitoring the means for positioning the optical axis, i.e. for example the motor or motors for adjusting the distance along the optical axis (Z) and for positioning the tables (B) and (C), monitoring the distance between the objective (2) of the microscope and the surface (S) under examination, acting on the above-mentioned laser illumination device (4), deciding on the images to be taken and being provided with at least one frame grabber card capable of operating with cameras in asynchronous operation, processing and analysing images, possibly emitting diagnostic information and archiving the results, is essentially characterised in that at least the following operations are carried out:

the product in motion including the surface (S) to be characterised is positioned in such a way as to allow said positioning to be repeated over time; in the case of a steel strip in motion, said strip is preferably applied to the surface of a roll by tension on said strip;

the microscope (1) is positioned in such a way that the optical axis (Z) is perpendicular to the plane including the surface (S) under examination on a microscopic scale; in the case of a steel strip (S) in motion passing onto a cylinder (6), the optical axis (Z) of the system preferably crosses the axis (7) of the cylinder orthogonally and is located in a arc segment enclosed between the first line of contact between the strip supporting the surface (S) and the cylinder (6) and the last line of contact between the strip supporting the surface (S) and the cylinder (6) in order to be positioned at a location on the roll where the product perfectly hugs the shape of the cylinder (6) and hence where the position of its surface is only a function of the position of the roll (6) and of the surface (S) itself;

the optical system is focussed in such a way as to obtain a sharp image;

the surface to be characterised is illuminated by means of an illumination device of the stroboscopic type, a stroboscopic laser illumination device (4) with an illumination time whose value is in accordance with the following calculation is preferably used:

$t = d/v \ \mu s$ where V is the linear velocity of the product in m/s d is the dimension of a camera pixel referred to the vision field, itself defined by the resolution required for the application, the dimension being given in µm, e.g. 1 µm, for a galvanised and alloyed surface (galvanneal);

and t is the time required for the product to travel d µm, the value of $t_{max}$ being defined in accordance with a rule of good practice which states that in order to freeze an object in motion, it must be illuminated for no more than the time necessary for it to have moved by a distance of ¼ of a pixel, this to ensure that a blurring effect in the obtained image is avoided;

a separate means is used to break the coherence of the beam used for illumination, this means preferably consisting in one or more diffusers;

at least one focussed image is taken;

images of the surface (3) are asynchronously acquired by means of an electronic frame grabber card; in the case of a steel strip in motion passing onto a cylinder, given that said cylinder always has an eccentricity linked to the design tolerances, the distance between the objective and the observation plane preferably varies according to a time cycle which is a function of the linear speed of motion at the inspection point, the system is positioned in such a way that the focussing distance is within the range of distance variation linked to the eccentricity of the cylinder so that the observation surface periodically passes through a focussing position;

the acquired images are processed and analysed in real time; the processing preferably consists at least of one operation aiming at freeing the captured image from all variation in the average level of illumination and/or from an effect of reflectivity linked to the product, preferably doing so in order to eliminate the background;

the image is analysed in real time by defining a criterion for determining the quality of the obtained image, e.g. the sharpness level of said image, the image is preferably divided into l*m zones, l and m are preferably comprised between 6 and 10 within the context of the analysis of a galvanised steel strip, each zone is assigned a sharpness parameter $n_i$, said parameter $n_i$ is evaluated for each zone, a total sharpness coefficient, which serves as a criterion for the acceptance or rejection of the image under consideration for its subsequent processing, is calculated;

a series of operations is performed in order to isolate and qualify the various objects present in the acquired image;

a first sorting operation is performed on the above-mentioned identified objects in consideration of the fact that an object is eliminated if it belongs to a blurred zone, i.e. a zone meeting the criterion $n_i$<predefined sharpness threshold L;

a second sorting operation is then performed on the remaining objects as a function of their surface and their dimensions, their respective number is weighted by means of the above-mentioned total sharpness coefficient by applying of the following formulae:

$p=(\Sigma p_i)/(l*m)$ where, if $n_i$<L, $p_i$=0, otherwise $p_i$=1 where $n_i$ is the calculated sharpness coefficient of the zone i;

L is the predefined sharpness threshold obtained by calibration in a laboratory or on the basis of a large number of images from which the background has been removed;

$p_i$ weighting coefficient of the zone i;

p total sharpness coefficient;

given that each number N of objects found in an image and determined as belonging to the same group is weighted with the total sharpness coefficient in such a way that:

$N_{final}=N/p$ where $N_{final}$ represents the final number of considered objects, taking into account the blurred zones of the analysed image;

the analysed image is eliminated if the total sharpness coefficient is less than a value determined as the minimum $p_{min}$; $p_{min}$ preferably being 0.5;

the values obtained during the preceding sorting operations are used to determine the characteristics of the inspected surface, for example the level of iron, powdering, the density of crystals.

Hereunder, an example of the calculation of the sharpness coefficient:

$$n_i = \sum_{k=0}^{H} \sum_{j=1}^{W} pixel_i[k][j-1] - pixel_i[k][j]$$

where $pixel_i[k][j]$=value of the pixel of line k and of column j in zone i.

In the context of the above-mentioned method, it is appropriate to give some precision regarding:

Focussing

The working distance is the distance between the surface under observation and the front face of the objective.

Two aspects are to be considered for focussing the system.

On the one hand, the system must initially be positioned in such a way that the optical axis is as perfectly perpendicular as possible to the surface to be observed.

On the other hand, given the small field depth available due to technical limitations, a correct image can only be obtained if the average level of the topography on a microscopic scale of the surface to be observed is within a relatively narrow interval, preferably in the middle, defined by the following values: working distance±half the field depth of the objective lens (2); nowadays, working distances between 10 mm and 30 mm with a field depth between 5 µm and 15 µm are technically possible. Thus, the distance between the surface and the sensor must be measured in a very accurate and very reproducible manner.

Moreover, the optical axis (Z) must be kept as perpendicular as possible to the surface (S) under observation.

Within the context of the present invention, these two positioning operations ((Z) axis and distance between the objective (2) and the surface (S)) are automatically performed. Initial positioning and at regular intervals is performed, especially when the installation is restarted and/or when the system is analysing too many blurred images (>50% for example) and/or a variation in the distance between the sensor and the product outside the variation range currently allowed by the technique, this corresponding to a field depth between 5 and 15 µm.

The positioning of the optical axis perpendicularly to the observation plane can be performed by means of 2 rotation tables and of the distance sensor. The method consists in positioning the system in such a way that, for a movement of each table, the distance signal is at the minimum of its value.

As far as the adjustment of the distance between the system and the cylinder is concerned, two methods are used. An absolute positioning on the basis of a focussing value predetermined in a laboratory and a more accurate positioning on the basis of a contrast analysis in the images obtained at different positions. Finally, images focussed as explained below are then taken, by adapting the illumination to the displacement mode of the inspected product.

Illumination

The product to be observed being in motion and the magnifications required being significant, an illumination device of the stroboscopic type is necessary in order to freeze the image and avoid a streaking effect on the latter. The illumination time cannot be greater than the time necessary to travel the distance corresponding in good practice to ¼ of a pixel. Considering, for example, a 768×576-pixel CCD camera coupled to a 20× objective with a long working distance (20 mm) and with a field depth of 7 μm, a 5× camera adaptation lens providing a view field of 250 μm×190 μm, for a product moving at a speed of 2 m/s and a field of 190 μm in length: ¼ of a camera pixel then corresponds to a view field of 0.08 μm.

Time necessary to travel this distance: $0.08*1/(2*10^6)=40$ ns

Considering the above-mentioned camera, for a product moving at a speed of 10 m/s and a field of 800 μm in length: ¼ of a camera pixel=0.35 μm.

Time necessary to travel this distance: $0.35*1/(10*10^6) =35$ ns.

Given the illumination times, a laser illumination device should consequently be used.

Two diffusers are also used, the first diffuser, on the one hand, widens the laser beam and breaks some of its coherence, and, on the other hand, avoids subjecting the input of the fibre to a beam that is too concentrated and hence damaging it. The second diffuser further widens the laser beam and likewise breaks some of its coherence. The coupling of the 2 diffusers and the optical fibre allows to break the coherence of the laser beam and hence to avoid an interference phenomenon at the level of the formed image.

The image acquisition, in the case of galvannealed sheets for instance, is of the asynchronous type by means of a frame grabber card.

The system being placed facing a cylinder with an eccentricity, the distance between the objective and the observation plane varies according to a time cycle that is a function of the line speed at the inspection point. Initially, the system is positioned in such a way that the focussing distance is preferably in the middle of the interval of distance variation linked to the eccentricity of the cylinder. In this way, the observation surface periodically passes through a focussing position. This position is continuously evaluated by a computer that triggers the image acquisition and the laser illumination pulse when the required distance is reached. The line speed and focussing periodicity allow a theoretical minimum acquisition frequency of 1 to 3 images per second.

Processing and Analysis of Images

The acquired images are processed and analysed in real time. In a first step, processing consists in removing all variation in the average level of illumination or of reflectivity of the product by elimination of the background. After the image has been divided into l*m zones, a sharpness parameter $n_i$ is then evaluated for each zone, and a total sharpness coefficient p is likewise calculated.

Finally, a series of operations allows to isolate and qualify the various objects present in the image. If an object belongs to a blurred zone ($n_i$<sharpness threshold L), it is eliminated from the counting process. The remaining objects are finally sorted as a function of their surface and their dimensions, and their respective number is weighted by the above-mentioned total sharpness coefficient p.

According to one embodiment of the process, which is the subject matter of the present invention, the disturbing influence of the background is eliminated by regularly re-evaluating the response of the system by calculating an image formed by attributing to each pixel the arithmetic average of the value of the corresponding pixels obtained over all the images under consideration, e.g. 50 images. This average corresponds to an image of the background common to all acquired images, and said average is subtracted pixel by pixel from each acquired image so as to standardise its illumination, which allows to use images that were taken even during the drift of certain constitutive components of the measurement system, such as the laser, the camera, . . . , this background is possibly calculated when the system is initialised or in a continuous manner, a new image being available every 0.5 s.

According to another embodiment of the process, which is the subject matter of the present invention, the image obtained is, on the one hand, divided into l*m zones of (768/l)*(576/m) pixels for example, after the illumination is standardised, and, on each of the zones i, a sharpness parameter $n_i$ is calculated using the transitions from one pixel to the adjacent pixel by summing the absolute values of the differences in level from one pixel to the adjacent pixel in order to obtain this sharpness parameter $n_i$, and said parameters $n_i$ are stored for subsequent use, and, on the other hand, a total sharpness coefficient p is established on the basis of a test on each zone, and finally each sharpness parameter $n_i$ is compared with a threshold value previously determined as a function of the inspected product, and the zone i is counted as 0 if the sharpness parameter $n_i$ is less than this threshold, and the zone i is counted as 1/(l*m) into the total sharpness coefficient p in the opposite case.

According to another preferred embodiment of the process, which is the subject matter of the present invention, the obtained image is binarised after the operation of eliminating the background on the basis of a maximum entropy method, which consists in optimising the quantity of information contained in the resulting image, which gives rise to a maximum number of objects which are distinguished and can be evaluated, and the objects present in the binarised image are determined and classified with a view to detecting the characteristic elements of the structure, such as the crystals, by establishing the list of the objects present in the resulting image.

According to yet another preferred embodiment of the process which is the subject matter of the present invention, in which a galvannealed steel strip is inspected, the surface area, the centre of gravity, the width and height of the inertia ellipse are calculated for each object; the following tests are carried out for each recorded object:

a. the object is eliminated if the centre of gravity of the object belongs to a zone considered as blurred on the basis that the above-established coefficient $n_i$ is less than a predefined threshold;

b. the object is eliminated if it is a horizontal line of a thickness of between 1 and 3 pixels, preferably one pixel thick, since it is considered to be corresponding to a parasitic image;

c. the object is counted as very large if the surface area of the object is greater than or equal to a predefined threshold referred to as "VeryBigArea$_{Thres}$", depending on the type of galvannealed steel;

d. the object is counted as large if the surface area of the object is greater than or equal to the predefined threshold "BigArea$_{Thres}$" and less than the threshold "VeryBigArea$_{Thres}$", depending on the type of galvannealed steel;

e. the object is counted as small if the surface area of the object is less than the predefined threshold "SmallArea$_{Thres}$", depending on the type of galvannealed steel;

f. if points c, d and e are not verified, the ratio (height of the object/width of the object) is determined and only the crystals with a ratio of between 0.2 and 0.5, preferably 0.3, are counted in order to determine the $\zeta$ crystals present in the image.

The $\zeta$ crystals have a minimum width of approximately 1 μm and can reach 20 μm in length, i.e. a ratio of 0.05. The crystals detected at the surface are those reflecting light in the correct direction for observation. However, not all these crystals are in a horizontal plane: they can be in planes of various orientations. Consequently, the ratio of their width to their length can vary when they are solely observed in a direction that is perpendicular to the surface.

A study of electronic images (large field depth) shows that the crystals are randomly aligned and that there is no preferential direction.

Accepting a ratio greater than 0.05 as an acceptance criterion allows to take account of crystals aligned in directions that are not exclusively within planes perpendicular to the optical axis of the system. This increases the number of detected crystals and improves the accuracy of the system. However, experience shows that this ratio cannot exceed 0.3 since other objects that are not $\zeta$ crystals are counted as such and scatter the measurement.

According to one embodiment of the process which is the subject matter of the present invention, the reflectance is measured at the location observed by the microscope, at least two values obtained for predetermined wavelengths are analysed, the ratio of the obtained values is preferably calculated.

This way of proceeding allows to simultaneously perform several types of on-line measurement (powdering, iron level, . . . ) on a galvanised steel strip in order to obtain the characteristics of the coating. On the one hand, the image obtained via a microscope is analysed, and the range of the latter is validated by using pyrometric measurements, which offer a very reliable means for extrapolating the results obtained on the basis of the microscopic image to the total width of the inspected strip.

Moreover, it has been observed that, when inspecting the surface of a galvannealed strip, it is difficult to apply the measurement process, which is the subject matter of the present invention owing to a saturation effect of the measurements due to an excessively high proportion of iron in the analysed coating alloy.

According to a preferred embodiment of the process which is the subject matter of the present invention, pyrometric measurements are carried out at wavelengths of 0.85±0.05 μm and 1.1±0.05 μm, and said measurement is used in order to validate the result obtained by image measurement.

The validation operation is to be understood as a means to declare that measurement by means of images relates to the zone (% Fe) in which the measurement method of the present invention has its application.

By way of example, the following procedure is adopted to establish the correlation with the percentage of iron and powdering.

Figure 4:
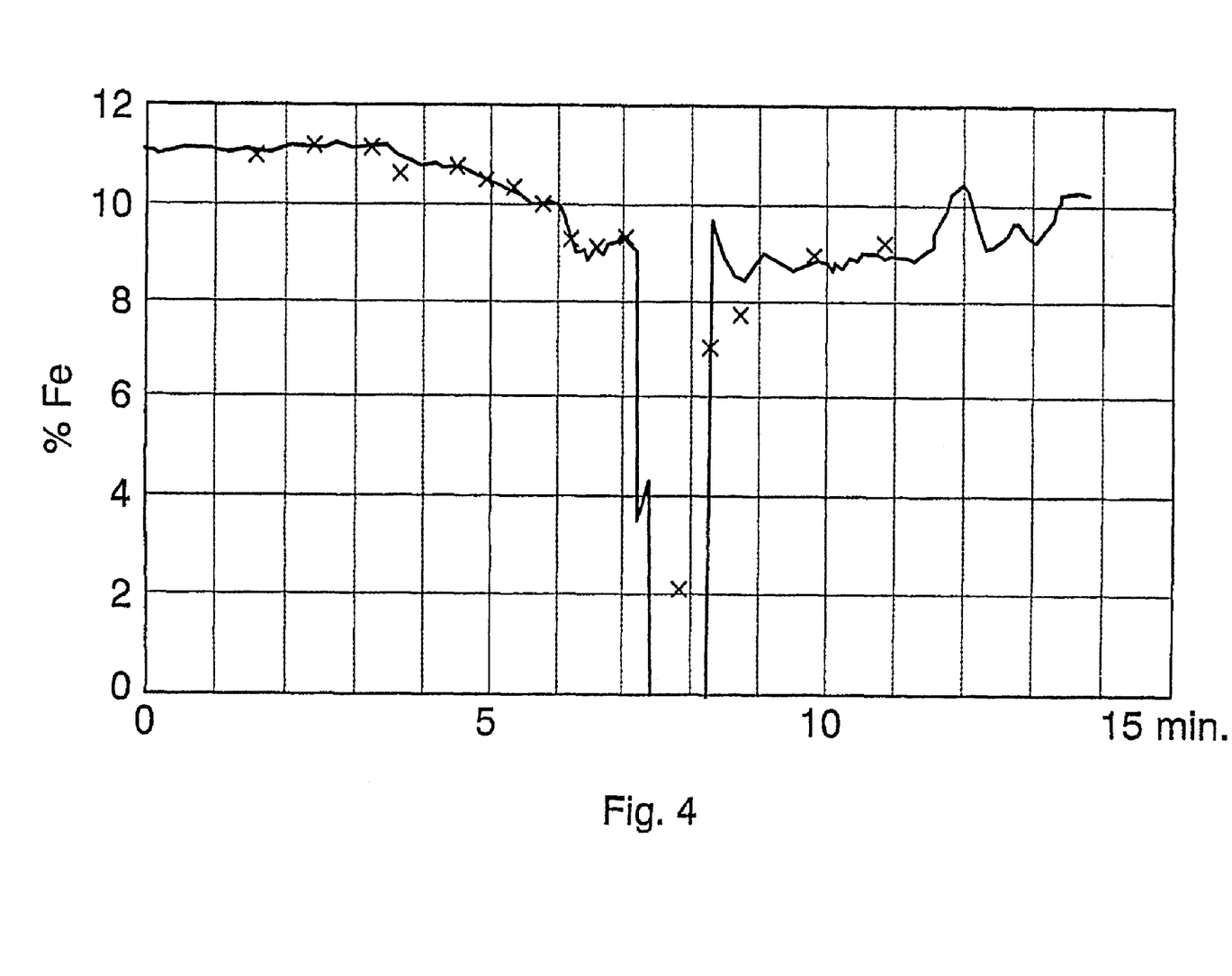
FIG. 4 shows the evolution, on the one hand, in the iron chemically metered onto a steel strip that is treated at various temperatures and, on the other hand, the iron percentage calculated in accordance with the method of the present invention.

FIG. 4 shows two graphs, one representing the percentage of iron chemically metered (values identified by X-shaped points) and the other derived from the calculation of the application of the method according to the present invention (values identified by a continuous line).

FIG. 4 is the representation of a measurement of the iron percentage, giving time as the abscissa and iron percentage as the ordinate.

It has been observed that for coatings with an iron percentage that is less than 7 or greater than 12, the process, which is the subject matter of the present invention as described above, is limited in its industrial implementation. This limitation is linked to a change in the inspected surface, namely:

at an iron level of less than 7%, an absence of objects that are linked to the crystals and that can be qualified in the above-mentioned manner is observed;

at a iron percentage greater than 12%, it is observed that the obtained images can no longer be differentiated from the images obtained at an iron content of 12%, the appearance of the surface of the product no longer being sensitive to an increase in the iron level.

Using the above-defined number of $\zeta$ crystals and the number of small objects (small area Thres), 2 correlations are established. The first with the iron percentage, the second with powdering. The correlation coefficients thus obtained are of the order of 0.84.

Small objects can be interpreted as $\zeta$ crystals or as an insufficiently alloyed surface area. The higher the iron percentage the greater the powdering and the more the number of $\zeta$ crystals at the surface decreases.

The measurement range for the iron percentage is of 7–12%. Outside this range, the associated optical sensor invalidates the measurement.

Device for Implementing the Process

The present invention also relates to a device for implementing the above-described process.

The device for implementing the process for the on-line characterisation of a surface in motion, in particular the surface of a steel strip in continuous motion that has undergone a galvannealing treatment, which is the subject matter of the present invention, according to one or other above-mentioned embodiments, is essentially characterised in that use is made of an industrial microscope equipped with an objective with a magnification of between 5× and 30× and a long working distance, i.e. greater than 10 mm, with the greatest possible depth of field, the minimum being equal to or greater than half the point-to-point roughness, in general 15 μm, comprising a camera adaptation lens with a magnification of between 2.5× and 5×, a CCD camera which, coupled to the objective and the adaptation lens, provides a view field with a width of between 125 μm and 2000 μm essentially with a spatial resolution of the system of at least 0.5 μm, the objective/lens assembly having to be adapted to the application as a function of the view field and of the required spatial resolution, said microscope comprising an illumination device of the bright-field and/or dark-field type constituted by a pulsed laser, e.g. a 532-nm YAG laser, with an energy that can be adjusted up to 10 mJ, with an illumination time that can be adjusted from 0 to 10 ns, comprising an optical fibre coupling the laser output to the illumination input of the microscope, said fibre being associated with 2 diffusers, one placed between the output of the laser and the input of the optical fibre, the other between the output of the optical fibre and the illumination input of the microscope, comprising a distance sensor (laser triangulation type) of high precision (at least 1/5 of the field depth) and of high repeatability (at least 1/5 of the field depth, preferably 1 µm at the minimum), placed at a distance of at least 10 mm from the surface of the strip and measuring variations within a range of at least −2 mm to +2 mm, said sensor being mounted in such a way that the zone observed by this sensor corresponds to the zone observed by the microscope, finally a motor mounted on the Z adjusting system (the Z axis corresponding to the optical axis of the system) of the microscope in order to correctly focus the system.

According to another embodiment of the device, which is the subject matter of the present invention, at least one motor-driven rotation table having a precision and a repeatability of at least 0.60°+/−0.1° is used in order to position the optical axis of the system in a plane that is perpendicular to the observation plane.

According to yet another embodiment of the device, which is the subject matter of the present invention, use is made of a sensor with a minimum required precision, in the case of the observation of the galvannealed coating, of 1/5 of the field depth, 1.4 µm for instance.

The following description is intentionally centred on the application of the process for the characterisation of a surface, which is the subject matter of the present invention, within the context of the inspection of a surface of a galvannealed steel strip. This choice aims at simplifying the description and is in no way a restriction as regards the application fields of the device in question.

The description will make reference to the attached drawings, in which certain elements are referenced.

According to a preferred embodiment of the device for implementing the process, which is the subject matter of the present invention, said device includes at least the following elements:

- an industrial microscope equipped with a 20× objective with a long working distance (20 mm) and a field depth of 7 µm, and with a 5× camera adaptation lens;
- a 768×576-pixel CCD camera which, coupled to the objective and the adaptation lens, provides a view field of 250×190 µm with a final spatial resolution of at least 0.5 µm;
- an illumination device of the bright-field and/or dark-field type constituted by a 532-nm pulsed YAG laser with an energy that can be adjusted up to 10 mJ, with an illumination time that can be adjusted from 0 to 10 ns, an optical fibre coupling the laser output to the illumination input of the microscope, 2 diffusers, preferably made of ground glass, one placed between the output of the laser and the input of the optical fibre, the other between the output of the optical fibre and the illumination input of the microscope; the first diffuser on the one hand widening the laser beam and breaking some of its coherence, thus avoiding subjecting the input of the fibre to a beam that is too concentrated and hence damaging it; the second diffuser further widening the laser beam and likewise breaking some of its coherence, the coupling of the 2 diffusers and of the optical fibre allowing to sufficiently break the coherence of the laser beam and hence avoid an interference phenomenon at the level of the image formed;
- a distance sensor (laser triangulation type) of high precision (at least 0.5 µm) and of high repeatability (at least 1 µm) placed at a distance of at least 10 mm from the surface of the steel strip in motion and measuring variations within a range of −2 to +2 mm, this sensor being obliquely mounted in order to ensure that the zone observed by this sensor corresponds to the zone observed by the microscope;
- a motor mounted on the Z adjusting system of the microscope in order to correctly focus the system;
- a motor-driven rotation table (B) serves as a support for the above-mentioned assembly associated with the industrial microscope, said motor-driven table has a precision and a repeatability of at least 0.6° in order to position the optical axis Z of the system in a plane that is perpendicular to the observation plane;
- a second motor-driven rotation table (C) with a precision and a repeatability of at least 0.6° supports the first table (B) in order to position the optical axis perpendicularly to the observation plane;
- a computer, which controls the assembly formed by the various parts A, B and C . . . and comprises a frame grabber card capable of working with cameras in asynchronous reset operation; an analog and digital input/output card with a resolution of 16 bits at the analog inputs; a card for controlling the 3 above mentioned motors; a data acquisition and processing program; the resolution of the input/output card being required for the distance signal supplied by the laser triangulation sensor should allow a precision of at least 1.4 µm, which is necessary for the correct positioning and good focussing of the image required by the small field depth of the objective used;
- a roll, on which the inspected product is applied by the tension effect imposed on the strip during its motion or by an appropriate separate means ensuring this function, said roll is positioned facing the assembly comprising the microscope and its two positioning tables, the optical axis of the system preferably passes through the centre of the cylinder and is positioned at a location on the roll where the product perfectly hugs the shape of the cylinder and hence where the position of its surface is a function only of the position of the roll and of the type of product;
- an optical sensor is associated with the microscope, the purpose of said sensor being, within the context of measuring the iron percentage and powdering of the galvannealed sheets, to validate the measurement obtained by image processing outside the range of 7%–12% of iron; the validation consists in coupling the information supplied, on the one hand, by analysis of the image obtained by the microscope and by the pyrometric measurements implementing the optical sensor.

The analysis of the pyrometric measurements gives complementary information on the structure, for example, and allows to validate the measurements obtained by means of the microscope over the entire width of the strip.

CONCLUSIONS

The process of the present invention thus allows to monitor galvannealing in two different ways. On the one hand, it allows to close the heating control loop by direct measurement of the iron level achieved in the coating examined, rather than by an indirect measurement of the temperature, as is the case in certain known conventional methods, and, on the other hand, it allows to locate the operation point of the galvannealing process as a function of the phase obtained at the surface and not of the achieved iron percentage, said iron percentage being obtained in the known methods by subsequent analysis of the product and not by the direct on-line measurement in the course of processing.

It will also be noted that, by adapting certain parameters, such as magnification (changing the objective and/or the intermediate lens), the camera (use of a colour camera, of a camera with a high spatial resolution), the illumination device (use of one or more lasers of different wavelengths for illumination), it is possible to implement the process for the characterisation of a surface in motion, which is the subject matter of the present invention, to other application fields, such as the qualification of deterministic roughness, the quantification of craters (shape, depth), the determination of spangle, the detection of oxides at the surface, monitoring of peeling (detection of cracks and of peeling of the oxide layer), the observation of hot-rolling cylinders to detect carbides, deep cracks, fine cracks and networks of cracks, which are usually more difficult to spot, in short, a significant number of defects and characteristics that can be observed on the surface of all types of materials.

The invention claimed is:

1. Process for the on-line characterisation of a surface (S) in motion, preferably a galvanised sheet, principally implementing:

a first assembly referred to as assembly A, consisting of at least one industrial microscope (1) equipped with an objective (2) having a long working distance, a camera adaptation lens, a camera (3) with an analog or digital output, an illumination device of the bright-field type and/or of the dark field type comprising a laser (4), a distance sensor (5) and a motor acting on the linear displacement along the (Z) axis, i.e. the displacement along the optical axis of the microscope in order to allow the correct focussing of the system, said assembly A being mounted on an assembly referred to as assembly D, which comprises two elements (B) and (C), said assembly D allowing to position the optical axis, i.e. (Z), perpendicularly to the plane containing the surface (S) under observation, said means preferably consisting in at least two motor-driven rotation tables (B) and (C) which, by their joint action, allow the optical axis (Z) of the microscope to be positioned perpendicularly to the observation plane containing the surface (S) under examination, the assembly D carrying the assembly A possibly being provided with an anti-vibration system, allowing to isolate said assembly from the metal frame, as found on an industrial continuous annealing and galvanisation line, which has to support it and is subjected to the various vibrations that are often present in this type of industrial process;

an assembly of means, preferably comprising a computer that allows to carry out at least the following operations:

monitoring the means for positioning the optical axis, i.e., for example, the motor or motors for adjusting the distance along the optical axis (Z) and for positioning the tables (B) and (C), monitoring the distance between the objective (2) of the microscope and the surface (S) under examination, acting on the above-mentioned laser illumination device (4), deciding on the images to be taken and being provided with at least one frame grabber card capable of operating with cameras in asynchronous operation, processing and analysing images, possibly emitting diagnostic information and archiving the results, characterised in that at least the following operations are carried out:

the product in motion comprising the surface (S) to be characterised is positioned in such a way as to allow said positioning to be repeated over time;

the microscope (1) is positioned in such a way that the optical axis (Z) is perpendicular to the plane comprising the surface (S) under examination on a microscopic scale;

the optical system is focussed in such a way as to obtain a sharp image;

the surface to be characterised is illuminated by means of an illumination device (4) of the stroboscopic type, preferably using a stroboscopic laser illumination device (4) with an illumination time whose value is in accordance with the following calculation:

$$t = d/V \, \mu s$$

where V is the linear velocity of the product in m/s d is the dimension of a camera pixel referred to the field of vision, itself defined by the resolution required for the application, the dimension being given in $\mu m$;

and t is the time required for the product to travel d $\mu m$, the value of $t_{max}$ being defined in accordance with a rule of good practice which states that in order to freeze an object in motion, it must be illuminated for no more than the time necessary for it to have moved by a distance of ¼ of a pixel, this in order to avoid a blurring effect in the image obtained;

a separate means is used to break the coherence of the beam used for illumination, this means preferably consisting in one or more diffusers;

at least one focussed image is taken;

images of the surface (S) are asynchronously acquired by means of an electronic frame grabber card;

the acquired images are processed and analysed in real time;

the image is analysed in real time, by defining a criterion for determining the quality of the obtained image;

a series of operations is performed in order to isolate and qualify the various objects present in the acquired image;

a first sorting operation is performed on the above-mentioned identified objects in consideration of the fact that an object is eliminated if it belongs to a blurred zone, i.e. a zone meeting the criterion $n_i$<predefined sharpness threshold;

a second sorting operation is then performed on the remaining objects as a function of their surface and their dimensions, their respective number is weighted by means of the above-mentioned total sharpness coefficient by application of the following formulae:

$$p = (\Sigma p_i)/(l*m)$$

where, if $n_i$<L, $p_i$=0, otherwise $p_i$=1 where $n_i$ is the calculated sharpness coefficient of the zone i;

L is the predefined sharpness threshold obtained by calibration in a laboratory or on the basis of a large number of images from which the background has been removed;

$p_i$ is the weighting coefficient of the zone i;

p is the total sharpness coefficient;

given that each number N of objects found in an image and determined as belonging to a same group is weighted with the total sharpness coefficient in such a way that:

$$N_{final} = N/p$$

where $N_{final}$ represents the final number of objects considered, taking into account the blurred zones of the analysed image;

the analysed image is eliminated if the total sharpness coefficient is less than a value determined as the minimum $p_{min}$; pmin preferably being 0.5;

the values obtained during the preceding sorting operations are used to determine the characteristics of the inspected surface.

2. Process according to claim 1, in the case of the implementation on a steel strip in motion, characterised in that the strip is positioned by applying said strip, by tension on the latter, to the surface of a roll.

3. Process according to claim 2, in the case of a steel strip (S) in motion passing onto a cylinder (6), characterised in that the microscope (1) is positioned in such a way that the optical axis (Z) of the system orthogonally crosses the axis (7) of the cylinder and is located in a arc segment enclosed between the first line of contact between the strip supporting the surface (S) and the cylinder (6) and the last line of contact between the strip supporting the surface (S) and the cylinder (6).

4. Process according to claim 2, in the case of a steel strip in motion passing onto a cylinder, given that said cylinder always has an eccentricity linked to the design tolerances, the distance between the objective and the observation plane varies according to a time cycle which is a function of the linear speed of motion at the inspection point, characterised in that images of the surface (S) are acquired by positioning the system in such a way that the focussing distance is within the interval of distance variation linked to the eccentricity of the cylinder so that the observation surface periodically passes through a focussing position.

5. Process according to claim 1, in relation to the processing and analysis of the images in real time, characterised in that it consists in at least one operation aiming at freeing the captured image from all variation in the average illumination level and/or from a reflectivity effect lihked to the product.

6. Process according to claim 5, characterised in that action is taken in order to eliminate the background.

7. Process according to claim 1, in relation to the criterion for determining the quality of the obtained image, characterised in that the image is divided into l*m zones, in that each zone is assigned a sharpness parameter ni, in that said parameter ni is evaluated for each zone, and in that a total sharpness coefficient, which serves as a criterion for the acceptance or rejection of the image under consideration for its subsequent processing, is calculated.

8. Process according to claim 7, in the context of the analysis of a galvannealed steel strip, characterised in that l and m are between 6 and 10.

9. Process according to claim 1, characterised in that the disturbing influence of the background is eliminated by regularly re-evaluating the response of the system by calculating an image formed by attributing to each pixel the arithmetic average of the value of the corresponding pixels obtained for all the images under consideration.

10. Process according to claim 1, characterised in that the image obtained is divided into l*m zones after the illumination is standardised, in that, for each of the zones i, a sharpness parameter ni is calculated by using the transitions from one pixel to the adjacent pixel by summing the absolute values of the differences in level from one pixel to the adjacent pixel in order to obtain this sharpness parameter ni, and in that said parameters ni are stored for subsequent use, in that a total sharpness coefficient p is established on the basis of a test on each zone, and finally in that each sharpness parameter ni is compared with a threshold value previously determined as a function of the inspected product, and in that the zone i is counted as 0 if the sharpness parameter ni is less than this threshold, and the zone i is counted as 1/(l*m) if the opposite is true.

11. Process according to claim 1, characterised in the obtained image is binarised after the background is eliminated on the basis of a maximum entropy method, which consists in optimising the quantity of information contained in the resulting image, which gives rise to a maximum number of objects which are distinguished and can be evaluated, and in that the objects present in the binarised image are determined and classified with a view to detecting the characteristic elements of the structure, such as the crystals, by establishing the list of the objects present in the resulting image.

12. Process according to claims 1, characterised in that a galvannealed steel strip is inspected, in that the surface area, the centre of gravity, the width and height of the inertia ellipse are calculated for each object, in that the following tests are carried out for each recorded object:

a. the object is eliminated if the centre of gravity of the object belongs to a zone considered as blurred on the basis that the above-established coefficient ni is less than a predefined threshold;

b. the object is eliminated if it is a horizontal line of a thickness between 1 and 3 pixels, preferably one pixel thick, since it is considered as corresponding to a parasitic image;

c. the object is counted as very large if the surface area of the object is greater than or equal to a predefined threshold referred to as "VeryBigAreaThres", depending on the type of galvannealed steel;

d. the object is counted as large if the surface area of the object is greater than or equal to the predefined threshold "BigAreaThres" and less than the threshold "VeryBigAreaThres", depending on the type of galvannealed steel;

e. the object is counted as small if the surface area of the object is less than the predefined threshold "SmallAreaThres" predefined, depending on the type of galvannealed steel;

f. if points c, d and e are not verified, the ratio (height of the object/width of the object) is determined and only the crystals with a ratio between 0.2 and 0.5, [preferably 0.3], are counted in order to determine the ζ crystals present in the image.

13. Process according to claim 1, characterised in that the reflectance is measured at the location observed by the microscope, at least two values obtained are analysed for predetermined wavelengths; the ratio of the values obtained is preferably calculated.

14. Process according to claim 13, characterised in that pyrometric measurements are carried out at wavelengths of 0.85±0.05 µm and 1.1±0.05 µm, and in that said measurement is used to validate the result obtained by image measurement.

15. Device for implementing the process for the on-line characterisation of a surface in motion, in particular the surface of a steel strip in continuous motion that has undergone a galvannealing treatment, according to claim 1, characterised in that use is made of an industrial microscope equipped with an objective with a magnification of between 5×and 30×and a long working distance, i.e. greater than 10 mm, with the greatest possible field depth, the minimum being equal to or greater than half the point-to-point roughness, in general 15 µm, comprising a camera adaptation lens with a magnification of between 2.5×and 5×, a CCD camera which, coupled to the objective and the adaptation lens, provides a view field with a width of between 125 µm and 2000 µm with essentially a spatial resolution of the system of at least 0.5 µm, the objective/lens assembly having to be adapted to the application as a function of the view field and of the required spatial resolution, said microscope comprising an illumination device of the bright-field type and/or dark-field type constituted by a pulsed laser with an energy that can be adjusted up to 10 mJ, with an illumination time that can be adjusted from 0 to 10 ns, comprising an optical fibre coupling the laser output to the illumination input of the microscope, said fibre being associated with 2 diffusers, one placed between the output of the laser and the input of the optical fibre, the other between the output of the optical fibre and the illumination input of the microscope, comprising a distance sensor (laser triangulation type) of high precision (at least 1/5 of the field depth) and of high repeatability (at least 1/5 of the field depth), preferably 1 gm at the minimum, placed at a distance of at least 10 mm from the surface of the strip and measuring variations within an interval of at least −2 mm to +2 mm, said sensor being mounted in such a way that the zone observed by this sensor corresponds to the zone observed by the microscope, finally a motor mounted on the Z adjusting system (the Z axis corresponding to the optical axis of the system) of the microscope in order to correctly focus the system.

16. Device according to claim 15, characterised in that at least one motor driven rotation table with a precision and a repeatability of at least 0.6° +/− 0.1° is used in order to position the optical axis of the system in a plane that is perpendicular to the plane of observation.

17. Device according to claim 15, characterised in that use is made of a sensor whose minimum required precision is 1/5 of the field depth, in the case of observation of the galvannealed coating.

18. Device according to claim 15, characterised in that it includes at least the following elements:
  an industrial microscope equipped with a 20× objective with a long working distance (20 mm) and a field depth of 7 µm, and with a 5× camera adaptation lens;
  a 768×576-pixel CCD camera which, coupled to the objective and the adaptation lens, provides a view field of 250×190 µm with a final spatial resolution of at least 0.5 µm;
  an illumination device of the bright-field type and/or dark-field type constituted by a 532-nm pulsed YAG laser with an energy that can be adjusted up to 10 mJ, with an illumination time that can be adjusted from 0 to 10 ns, an optical fibre coupling the laser output to the illumination input of the microscope, 2 diffusers, preferably made of ground glass, one placed between the output of the laser and the input of the optical fibre, the other between the output of the optical fibre and the illumination input of the microscope; the first diffuser on the one hand widening the laser beam and breaking some of its coherence, thus avoiding subjecting the input of the fibre to a beam that is too concentrated and hence damaging it; the second diffuser further widening the laser beam and likewise breaking some of its coherence, the coupling of the 2 diffusers and of the optical fibre allowing to sufficiently break the coherence of the laser beam and hence avoid an interference phenomenon at the level of the image formed;
  a distance sensor (laser triangulation type) of high precision (at least 0.5 µm) and of high repeatability (at least 1 µm) placed at a distance of at least 10 mm from the surface of the steel strip in motion and measuring variations within an interval of −2 to +2 mm, this sensor being mounted obliquely to ensure that the zone aimed at by this sensor corresponds to the zone observed by the microscope;
  a motor mounted on the Z adjusting system of the microscope in order to correctly focus the system;
  a motor-driven rotation table (B) serves as a support for the above-mentioned assembly associated with the industrial microscope, said motor-driven table has a precision and a repeatability of at least 0.6° in order to position the optical axis Z of the system in a plane that is perpendicular to the observation plane;
  a second motor-driven rotation table (C) with a precision and a repeatability of at least 0.60° supports the first table (B) in order to position the optical axis perpendicularly to the observation plane;
  a computer, which controls the assembly formed by the various parts A, B and C... and comprises a frame grabber card capable of working with cameras in asynchronous reset operation; an analogue and digital input/output card with a resolution of 16 bits at the analog inputs; a card for controlling the 3 above-mentioned motors; a data acquisition and processing program; the resolution of the input/output card being required for the distance signal supplied by the laser triangulation sensor should allow to reach a precision of at least 1.4 µm, which is necessary for the correct positioning and good focussing of the image required by the small field depth of the objective used;
  a roll, on which the inspected product is applied by the tension effect imposed on the strip during its motion or by an appropriate separate means ensuring this function, said roll is positioned facing the assembly comprising the microscope and its two positioning tables, the optical axis of the system preferably passes through the centre of the cylinder and is positioned at a location on the roll where the product perfectly hugs the shape of the cylinder and hence where the position of its surface is a function only of the position of the roll and of the type of product;
  an optical sensor is associated with the microscope, the purpose of said sensor, within the context of measuring the iron percentage and the powdering of the galvannealed sheets, being to validate the measurement obtained by image processing outside the interval of 7%–12% of iron; the validation consists in coupling the information supplied, on the one hand, by analysis of the image obtained by the microscope and by the pyrometric measurements implementing the optical sensor.

* * * * *